Figure 1:
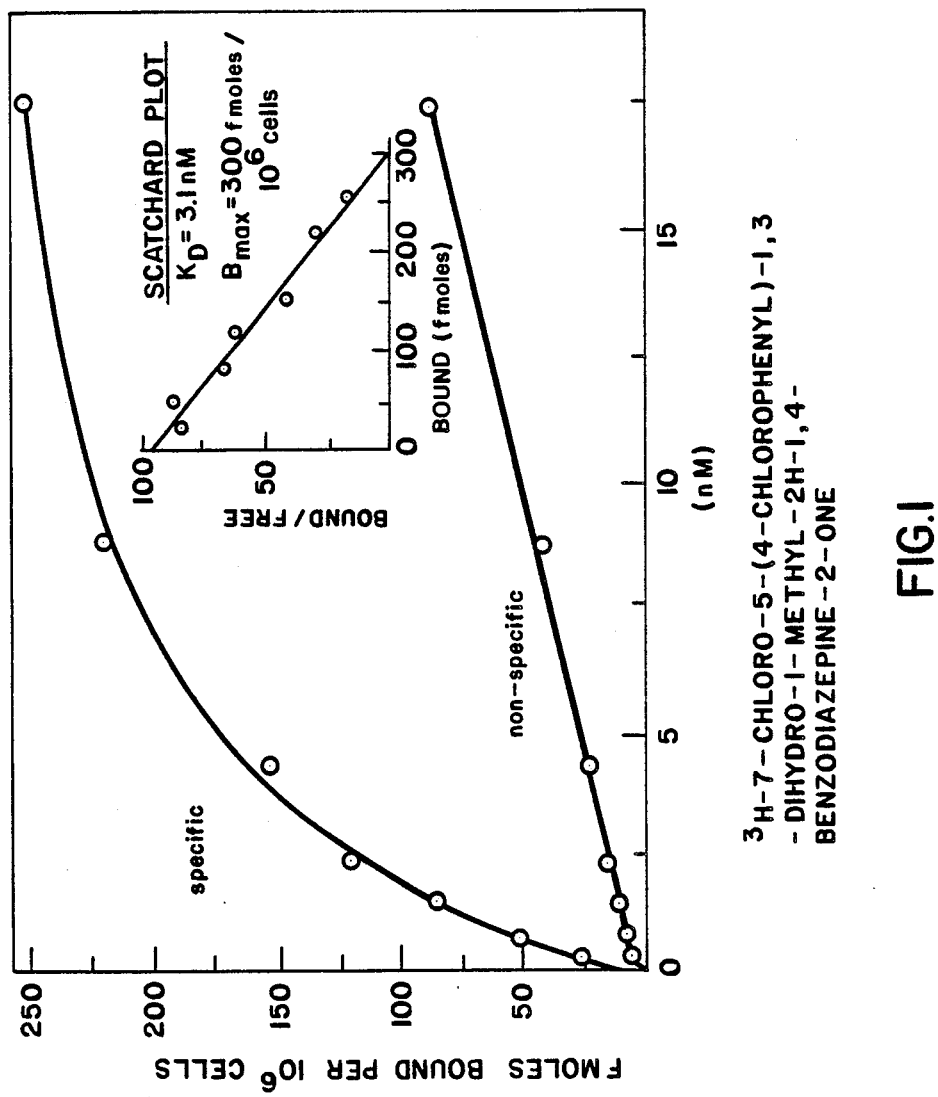

United States Patent [19]

Morgan et al.

[11] Patent Number: 4,898,861
[45] Date of Patent: Feb. 6, 1990

[54] METHOD FOR INHIBITING THE PROLIFERATION OF TUMOR CELLS

[75] Inventors: James I. Morgan, Upper Montclair; Sydney Spector, Livingston, both of N.J.; James K. T. Wang, New York City, N.Y.

[73] Assignee: Hoffmann-La Roche Inc., Nutley, N.J.

[21] Appl. No.: 237,649

[22] Filed: Aug. 29, 1988

Related U.S. Application Data

[63] Continuation of Ser. No. 30,932, Mar. 26, 1987, abandoned, which is a continuation of Ser. No. 655,653, Sep. 28, 1984, abandoned, which is a continuation-in-part of Ser. No. 524,169, Aug. 17, 1983, abandoned.

[51] Int. Cl.$^4$ ............................................. A61K 31/55
[52] U.S. Cl. ................................................... 514/221
[58] Field of Search ........................................ 514/221

[56] References Cited

PUBLICATIONS

Chemical Abstracts 98:83311Z (1983) abstracting Igaku W. Ayumi 1982 reference.
Chemical Abstracts 94:96270 C (1981).

*Primary Examiner*—Jerome D. Goldberg
*Attorney, Agent, or Firm*—Jon S. Saxe; Bernard S. Leon; A. Kate Huffman

[57] ABSTRACT

A method of inhibiting the proliferation of tumor cells is disclosed which comprises the treatment of such tumor cells with a benzodiazepine having a selective affinity to bind peripheral binding sites on the tumor cell in order to induce non-proliferation of said tumor cells.

8 Claims, 4 Drawing Sheets

METHOD FOR INHIBITING THE PROLIFERATION OF TUMOR CELLS

This application is a continuation of application Ser. No. 030,932, filed Mar. 26, 1987, now abandoned, which is a continuation of Ser. No. 655,653, filed Sept. 28, 1984, now abandoned, which is a continuation-in-part of Ser. No. 534,169, filed Aug. 17, 1983, now abandoned.

DESCRIPTION OF THE INVENTION

There is disclosed a method of inhibiting the proliferation of tumor cells which comprises treatment of such tumor cells with a benzodiazepine having a selective affinity to bind peripheral binding sites on the tumor cell, said tumor cell having specific, saturable, peripheral binding sites.

The benzodiazepines useful in the above method are ones having an affinity for the peripheral binding site on tumor cells having such a binding site. Further, an especially preferred class of benzodiazepines are those of the formula

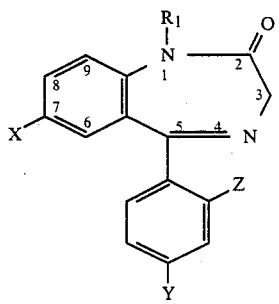

wherein $R_1$ is $C_1$ to $C_3$ lower alkyl, $C_2$ to $C_3$ alkenyl or $C_2$ to $C_3$ alkynyl; Y is halogen, hydroxy or lower alkoxy; X is hydrogen or halogen and Z is hydrogen or halogen.

The compounds of formula I are preferred since they exhibit a selective affinity for the peripheral binding sites on tumor cells.

The specific binding of benzodiazepines has been observed in many tissues and cell types and can be pharmacologically separated into two classes. The first class is represented by binding of the central-type receptors of the brain whcih are thought to mediate the known pharmacological effects of the benzodiazepines. The other calss of receptor is represented by the peripheral-type binding site found on a variety of tissues and cell, for example, kidney, heart, platelets, mast cells, lymphocytes and many cell lines.

Clarke and Ryan, Nature, 287, 160–161 (1980) have reported that some benzodiazepines inhibit proliferation of Swiss 3T3 cells in culture and further induce the differentiation of Friend erythroleukemia cells. Most of the compounds utilized in their study, however, were selective for central-type receptors displaying $ED_{50}$ values substantially greater than 100 μM. The two most active compounds reported by Clarke and Ryan exhibited substantial binding to both peripheral and central receptor sites (not reported by Clarke and Ryan), the most active being diazepam with an $ED_{50}$ of about 30 μM. The study, however, did not determine benzodiazepine binding constants and, therefore, stated that no correlation could be made between such constants and the antiproliferative effects seen. The article did ascribe the activity of the compounds to their lipophilic nature. Further, Matthew et al. Proc. Natl. Acad. Sci. USA, 78, p.p. 3935–3939, June 1981 have reported the use of various benzodiazepines to induce melanogenic differentiation in B16/C3 melanoma cells.

Applicants have found, however, that a correlation does exist between various benzodiazepines' binding affinities for peripheral receptors and their antiproliferative activity on tumor cells. Further it has been found that some of these compounds induce terminal differentiation of the tumor cells to the normal state but that the compound's ability to induce differentiation is not correlated to their relative affinity to bind to the peripheral site and thus the ability to cause differentiation is a separate function not associated with the benzodiazepines' ability to inhibit proliferation of tumor cells.

The antiproliferative effect is paralleled by the ability of the benzodiazepines to inhibit the incorporation of thymidine in the most studied system, i.e. thymoma cells. Thus by measuring levels of tritiated thymidine in the cell system a correlation can be made between thymidine uptake and antiproliferative activity on tumor cells.

Further differentiation of the tumor cells to the normal state is measured by the ability of the cell studied to make hemoglobin, i.e. to function as a normal blood cell.

The preferred class of benzodiazepenes are ones which are known in the art along with methods to produce same. Examples of such prior art teaching include for example, U.S. Pat. No. 3,336,295. This patent is incorporated by reference herein in so far as it will enable one skilled in the art to make these known compounds.

The benzodiazapines utilized in the present method may be administered by a variety of routes, most preferably by oral means. Another method which is useful entails treatment of marrow cells in vitro followed by transplantation of the cells in the host. Such methods are known in the art or may be modified by one skilled in the art in the present circumstances, see, for example, Sarna et al., Cancer Treatment Reports, 66, No. 2, February 1982 or Appelhaum et al., Journal of Clinical Oncology, 1, No. 7, July 1983. An effective dose of the preferred benzodiazapines may range from about 10 mg/kg to about 50 mg/kg per day but may be adjusted to higher doses if necessary given the patient's condition, body weight and responsiveness to treatment.

EXAMPLE 1

Thymoma cells, AKR mouse thymoma line, BW 5147.6.1.4.Oua$^r$.1.(Cell Distribution Center, Salk Institute, San Diego, Calif.), were grown in Iscove's Modified Dulbecco's Medium (IMDM) containing 5 percent fetal calf serum, collected by centrifugation at 100×g and washed in Balanced Glucose Salt (BGS) buffer, the composition of which is: KCl, 5.0 mM; NaCl, 120.0 mM; $Na_2HPO_4$, 5.0 mM; Tris, 5.0 mM; $CaCl_2$, 0.6 mM; $MgSO_4$, 1.0 mM and glucose, 5.5 mM with a final pH of 7.4. Incubation and binding of tritiated 7-chloro-5-(4-chlorophenyl)-1,3-dihydro-1-methyl-2H-1,4-benzodiazepin-2-one to thymoma cells was carried out in BGS buffer at 0° C. for 40 minutes with the indicated concentrations of labeled ligand. To assay the binding, the rapid filtration method was utilized as outlined in the article of Taniguchi et al., Life Science, 27, 171–178 (1980) and 10 μM of unlabeled diazepam was used as the competitive inhibitor of binding to determine the nonspecific binding. A Saturation and Scratchard plot of the binding data using least square fit to define the regression line (r=0.97) was utilized (FIG. 1 and Insert). Analysis of the saturation plot showed a single class of binding sites with a $K_D$ of 4.4±1.1 nM (mean±s.e., n=5) and the maximum amount of ligand bound (Bmax) was 477±98 fmoles per $10^6$ cells (mean±s.e., n=5). That a peripheral binding site on the thymoma cells is involved was demonstrated by the ability of the unlabeled 7-chloro-5-(4-chlorophenyl)-1,3-dihydro-1-methyl-2H-1,4-benzodiazepin-2-one at 200 nM to completely inhibit the binding of tritiated diazepam, a ligand which binds both peripheral and central sites whereas clonazepam, a central site selective benzodiazepine, did not inhibit diazepam binding even at 10 μM final concentration.

The binding of the tritiated 7-chloro-5-(4-chlorophenyl)-1,3-dihydro-1-methyl-2H-1,4-benzodiazepin-2-one to the thymoma cells reached a plateau after 30 minutes of incubation at 0° C. and dissociated with a $t_\frac{1}{2}$ of 17 minutes when an excess (10 μM) of unlabeled diazepam was added to the incubation.

EXAMPLE 2

Figure 2:
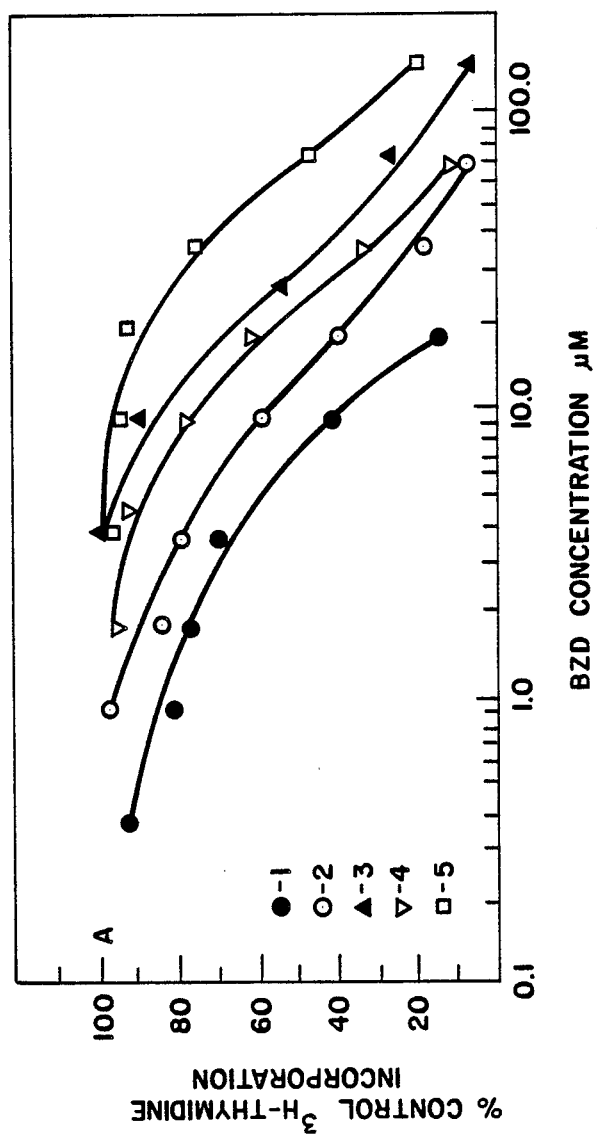
Figure 3:
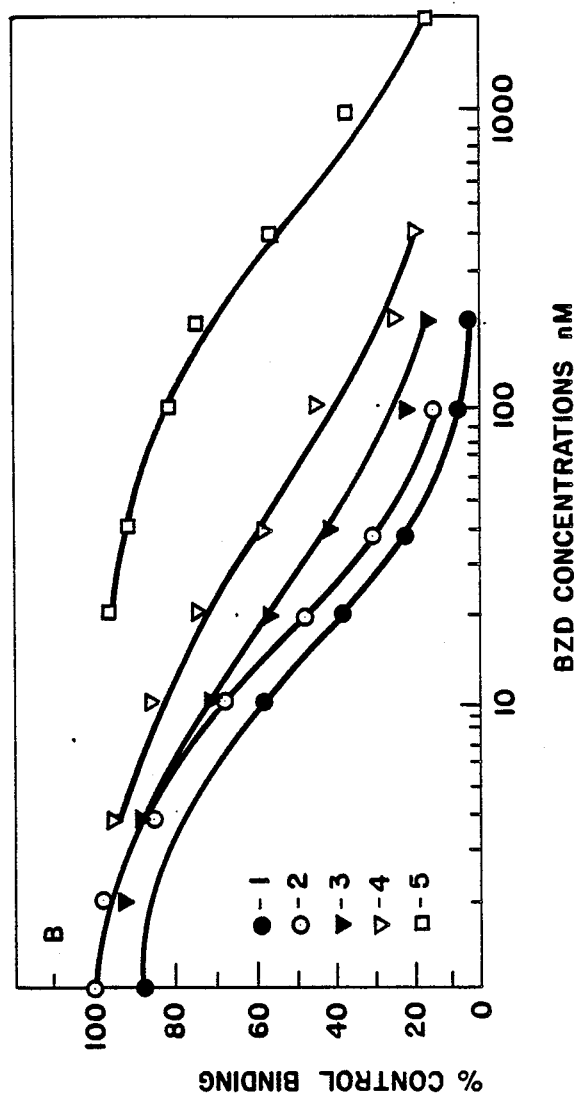

The following benzodiazepines were tested in a dose-response relationship for (A) inhibiting tritiated thymidine incorporation by thymoma cells and (B) inhibiting tritiated 7-chloro-5-(4-chlorophenyl)-1,3-dihydro-1-methyl-2H-1,4-benzodiazepin-2-one binding to thymoma cells (FIGS. 2 and 3). The compounds and symbols utilized in the figures were:
1. 1-allyl-7-chloro-5-(p-chlorophenyl)-3H-1,4-benzodiazepin-2(1H)-one (●);
2. 7-chloro-5-(4-methoxyphenyl)-1-methyl-3H-1,4-benzodiazepin-2(1H)-one (°);
3. 5-(4-chlorophenyl)-7-fluoro-1-methyl-3H-1,4-benzodiazepin-2(1H)-one (□);
4. diazepam (▽) and
5. 1-methyl-5-(4-fluorophenyl)-3H-1,4-benzodiazepin-2(1H)-one (□).

(A) For the tritiated thymidine assay, cells were seeded in 96-well tissue culture clusters (Coster Co.) at $1 \times 10^5$ cells per well for the 22 hour assay or $1 \times 10^4$ cells per well for the 44 hour assay. The benzodiazepines were diluted from ethanol stock solutions into Iscove's Modified Dulbecco's Medium and then directly into the wells to yield the appropriate final concentration in a total volume of 200 ul. The ethanol concentration was never higher than 0.4 percent and controls containing the appropriate ethanol concentrations were included in the experiments to show that ethanol at those concentrations had no effect on proliferation of the thymoma cells. After either 22 hours or 44 hours of incubation at 37° C., the cells were pulsed for 2 hours with 1 μCi/250 μl of tritiated thymidine and 0.5 μM of unlabeled thymidine. Cells were then harvested and washed over glass fiber filters by a Microharvester ™ (Bellco Glass, Inc.). The filters were dried and placed in 4 ml of Aquasol (New England Nuclear) in minivials for scintillation counting. Control counts were expressed as 100 percent and all other counts as percent of control. $ED_{50}$ was calculated as the dose required to reduce the tritiated thymidine uptake to 50 percent of control. The results are plotted in FIG. 2.

(B) Binding assays were performed as in Example 1. Thymoma cells were incubated with tritiated 7-chloro-5-(4-chlorophenyl)-1,3-dihydro-1-methyl-2H-1,4-benzodiazepin-2-one (0.8 nM) with or without various concentrations of the five benzodiazepines of Part (A), Example 2, in Balanced Glucose Salt buffer at 0° C. for 40 minutes. Control binding was defined as specific binding in the absence of any unlabeled benzodiazepines and was expressed as 100 percent. The $IC_{50}$ was calculated as the dose of benzodiazepine which inhibited tritiated 7-chloro-5-(4-chlorophenyl)-1,3-dihydro-1-methyl-2H-1,4-benzodiazepin-2-one binding by half.

EXAMPLE 3

The following benzodiazepines were tested for a correlation between their binding constants and their $ED_{50}$ in inhibiting tritiated thymidine uptake by thymoma cells. The binding constants ($IC_{50}$) and $ED_{50}$ in inhibiting tritiated thymidine uptake were determined following the procedures of Example 2. Values for the compounds are plotted in FIG. 4, each value being the mean of at least four experiments. The benzodiazepines tested and related numbers in FIG. 4 (in parentheses) were as follows:
1. Diazepam (12)
2. 7-chloro-5-(2-chlorophenyl)-1,3-dihydro-1-methyl-2H-1,4-benzodiazepin-2-one(5)
3. 1,3-dihydro-1-methyl-5-phenyl-2H-1,4-benzodiazepin-2-one(8)
4. 5-(2-chlorophenyl)-1-methyl-3H-1,4-benzodiazepin-2(1H)-one(7)
5. 5-(4-chlorophenyl)-1-methyl-3H-1,4-benzodiazepin-2(1H)-one(11)
6. 1-methyl-5-(4-fluorophenyl-3H-1,4-benzodiazepin-2(1H)-one(9)
7. 5-(4-chlorophenyl)-4,5-dihydro-7-fluoro-1,4-dimethyl-3H-1,4-benzodiazepin-2(1H)-one(10)
8. 5-(4-chlorophenyl)-7-fluoro-1-methyl-3H-1,4-benzodiazepin-2(1H)-one(4)
9. 7-chloro-5-(4-methoxyphenyl)-1-methyl-3H-1,4-benzodiazepin-2(1H)-one(14)
10. 7-chloro-5-(2,4-dichlorophenyl)-1-methyl-3H-1,4-benzodiazepin-2(1H)-one(3)
11. 7-chloro-5-(2,4-dichlorophenyl)-4,5-dihydro-1-methyl-3H-1,4-benzodiazepin-2(1H)-one(13)
12. 1-allyl-7-chloro-5-(p-chlorophenyl)-3H-1,4-benzodiazepin-2(1H)-one(15)
13. 7-chloro-1-ethyl-5-(p-chlorophenyl)-3H-1,4-benzodiazepin-2(1H)-one(1)
14. 7-chloro-5-(2,6-dichlorophenyl)-1,3-dihydro-1-methyl-2H-1,4-benzodiazepin-2-one(6)
15. 7-chloro-5-(4-chlorophenyl)-1,3-dihydro-1-methyl-2H-1,4-benzodiazepin-2-one(2)

Figure 4:
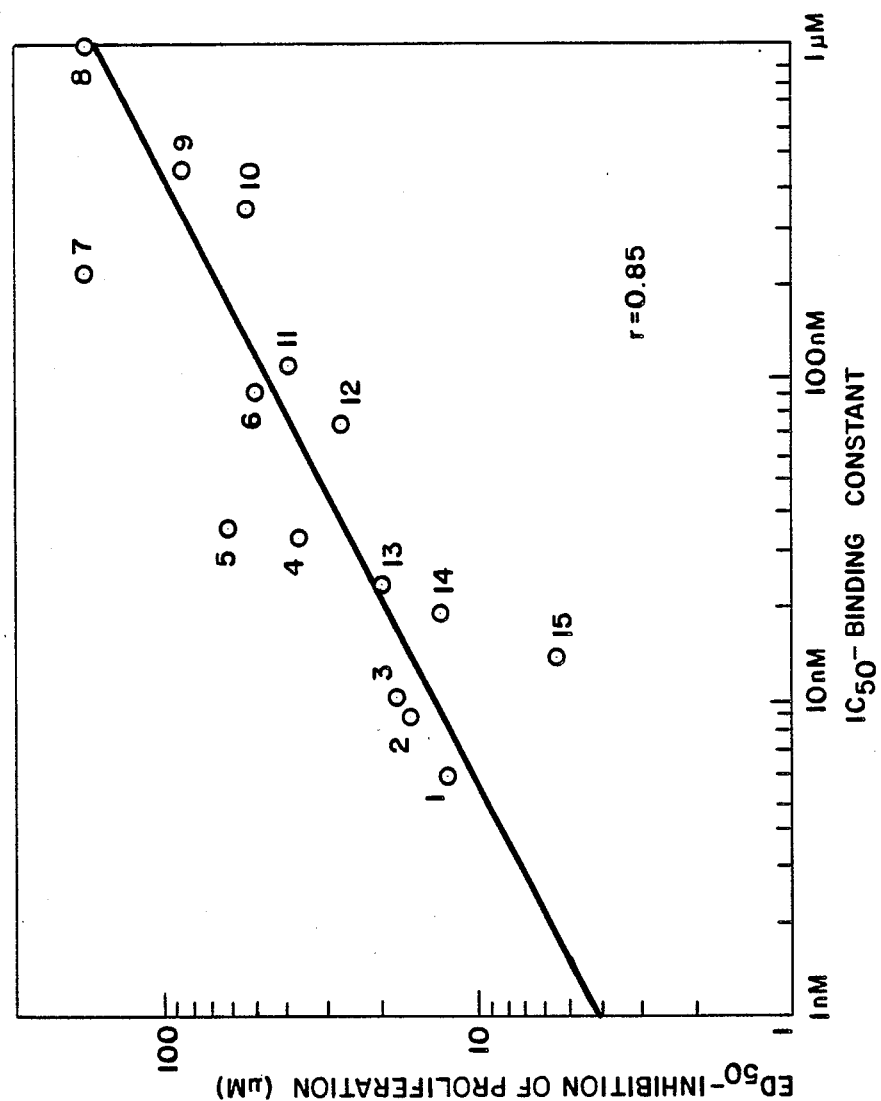

The plot in FIG. 4 utilizes the numbers assigned above for the respective benzodiazepines.

The $IC_{50}$ values spanned about two orders of magnitude, ranging from 6 nM to 1 μM. When the compounds were included in the thymoma cell culture at μM concentrations, they dramatically reduced the cell number during subsequent days of culture without being cytotoxic (as determined by trypan blue staining). The thymidine uptake inhibitory effect appeared after 8 hours (roughly the doubling time of the cells) of incubation and was marked after 22 hours. The inhibition was reversible by diluting the cells into fresh medium which contained no benzodiazepines. All of the benzodiazepines inhibited tritiated thymidine incorporation in a dose dependent manner (FIG. 3), the half effective concentrations ($ED_{50}$) required ranged from 6 μM to 180 μM. These values were ranked with the $IC_{50}$ values of binding and plotted on log-log scale (FIG. 4) resulting in a positive and highly significant correlation with the coefficient of correlation being r=0.85 (p<0.001).

EXAMPLE 4

A DS 19 Friend erythroleukemia cell line (FEL) was utilized as the model for studying the effects of various benzodiazepines on cellular differentiation. The Friend lines were derived from mouse (DBA/2) spleen cells infected by the Friend virus complex. The FEL cells are a widely used model system for studying differentiation. To assess the differentiation of FEL cells the induction of synthesis of hemoglobin was used as the marker to demonstrate terminal differentiation. The protocol utilized consisted of the benzidine staining method. Cells were seeded at $1 \times 10^4$ ml and incubated with inducers in Coster Culture Clusters (24 cells) for 5 days. On the 5th day, two hundred (200) μl aliquots of cells were mixed with 100 μl of 0.2% benzidine dihydrochloride in 0.5N acetic acid with 1% of 30% $H_2O_2$. Cells that stained blue were scored in a hemacytometer as a % of total cell number.

Of twenty five (25) of the benzodiazepines tested it was observed that sixteen induced differentiation (weakly to strongly active) in a concentration-dependent manner. The concentration of each compound required to induce 50%, 20% or 10% of the FEL cells along with the half-maximal concentrations for each compound required to inhibit 50% of the binding of 7-chloro-5-(4-chlorophenyl)-1,3-dihydro-1-methyl-2H-1,4-benzodiazepine-2-one to the FEL cells ($IC_{50}$) is listed in the following table:

TABLE

| Compound | $ED_{50}(\mu M)$ | $IC_{50}(nM)$ |
|---|---|---|
| 1. (+)-5-(2-fluorophenyl)-1,3-dihydro-1,3-dimethyl-7-nitro-2H—1,4-benzodiazepin-2-one | 9 | 1097 |
| 2. 7-chloro-1,3-dihydro-5-(4-hydroxyphenyl)-1-methyl-2H—1,4-benzodiazepin-2-one | 20 | 100 |
| 3. 7-chloro-5-(4-methoxyphenyl)-1-methyl-3H—1,4-benzodiazepin-2-one | 33 | 15 |
| 4. diazepam | 55 | 79 |
| 5. 7-chloro-1,3-dihydro-3-hydroxy-1-methyl-5-phenyl-2H—1,4-benzodiazepin-2-one | 80 | 236 |
| 6. 1,3-dihydro-1-methyl-5-phenyl-2H—1,4-benzodiazepin-2-one | 80 | 704 |

| Compound | $ED_{20}(\mu M)$ | $IC_{50}(nM)$ |
|---|---|---|
| 7. 5-(4-chlorophenyl)-7-fluoro-1-methyl-3H—1,4-benzodiazepin-2(1H)—one | 34 | 13 |
| 8. 5-(4-chlorophenyl)-1-methyl-3H—1,4-benzodiazepin-2(1H)—one | 30 | 54 |
| 9. (−)-5-(2-fluorophenyl)-1,3-dihydro-1,3-dimethyl-7-nitro-2H—1,4-benzodiazepin-2-one | 86 | 1037 |
| 10. 7-chloro-5-(4-chlorophenyl)-1,3-dihydro-1-methyl-2H—1,4-benzodiazepin-2-one | 28 | 6 |
| 11. 7-chloro-5-(4-chlorophenyl)-3-hydroxy-1,3-dihydro-1-methyl-2H—1,4-benzodiazepin-2-one | 45 | 20 |
| 12. 1-methyl-5-(4-fluorophenyl)-3H—1,4-benzodiazepin-2(1H)—one | 100 | 327 |

| Compound | $ED_{10}(\mu M)$ | $IC_{50}(\mu M)$ |
|---|---|---|
| 13. 5-(2-fluorophenyl)-1,3-dihydro-1-methyl-7-nitro-2H—1,4-benzodiazepin-2-one | 32 | 80 |
| 14. 5-(4-chlorophenyl)-1-methyl-7-nitro-3H—1,4-benzodiazepin-2(1H)—one | 60 | 34 |
| 15. 5-(2-chlorophenyl)-1-methyl-3H—1,4-benzodiazepin-2(1H)—one | 60 | 175 |
| 16. 7-chloro-5-(2-chlorophenyl)-1,3-dihydro-1-methyl-2H—1,4-benzodiazepin-2-one | 60 | 11 |

All of the benzodiazepines active in inducing differentiation bind to the peripheral-type benzodiazepine sites with affinities that ranged from 6 nM to 1 μM but there was no obvious correlation between the binding constants and the concentrations needed to induce differentiation. Indeed the two phenomena of induction of differentiation and binding to the peripheral-type benzodiazepine sites could be dissociated by the stereoisomers nature of the former and lack of stereospecificity of the latter. The two stereisomers set forth in Table 1 with an optical chiral center at the methyl substitute 3-position (Compounds 1 and 9) exhibited equivalent $IC_{50}$'s of about 1 μM whereas the (+)S isomer was the most potent inducer tested ($ED_{50}$=9 μM) and the (−)R isomer was classified as moderately active ($ED_{20}$=86 μM).

What is claimed:

1. A method for treating a patient afflicted with tumor cells having specific, saturable peripheral binding sites which comprises orally administering to the patient a benzodiazepine having a selective affinity to bind to the peripheral binding sites on the tumor cells, which cells are sensitive to treatment with the benzodiazepine, said benzodiazepine having the formula

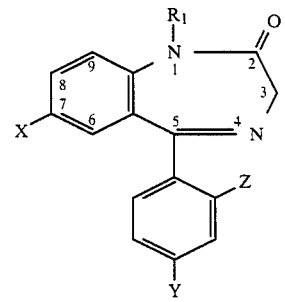

wherein $R_1$ is $C_1$ to $C_3$ alkyl, $C_2$ to $C_3$ alkenyl or $C_2$ to $C_3$ alkynyl; Y is halogen, hydroxy or lower alkoxy; X is halogen and Z is halogen or hydrogen, in a daily dose between about 10 mg/kg of body weight of the patient and about 50 mg/kg of body weight of the patient which is effective for inhibiting the proliferation of said tumors cells.

2. The method of claim 1 wherein Y is halogen.
3. The method of claim 2 wherein X is halogen.
4. The method of claim 1 wherein $R_1$ is methyl, ethyl, or allyl.
5. The method of claim 4 wherein Y is Cl or methoxy.
6. The method of claim 5 wherein Z is Cl.
7. The method of claim 1 wherein the benzodiazepine is selected from the group consisting of 7-chloro-5-(4-methoxyphenyl)-1-methyl-3H-1,4-benzodiazepine-(1H)-one; 7-chloro-5-(2,4-dichlorophenyl)-1-methyl-3H-1,4-benzodiazepin-2(1H)-one; 7-chloro-5-(2,4-dichlorophenyl)-4,5-dihydro-1-methyl-3H-1,4-benzodiazepine-(1H)-one; 1-allyl-7-chloro-5-(p-chlorophenyl)-3H-1,4-benzodiazepine-(1H)-one; 7-chloro-1-ethyl-5-(p-chlorophenyl)-3H-1,4-benzodiazepine-(1H)-one; and 7-chloro-5-(4-chlorophenyl)-1,3-dihydro-1-methyl-2H-1,4-benzodiazepine-one.

8. The method of claim 1 wherein the benzodiazepine selected is 1-allyl-7-chloro-5-(p-chlorophenyl)-3H-1,4-benzodiazepin-2(1H)-one.

* * * * *